(12) United States Patent
Yang et al.

(10) Patent No.: US 11,391,749 B2
(45) Date of Patent: Jul. 19, 2022

(54) GENE CHIP AND GENE DETECTION DEVICE

(71) Applicant: BOE TECHNOLOGY GROUP CO., LTD., Beijing (CN)

(72) Inventors: Song Yang, Beijing (CN); Ming Zhu, Beijing (CN); Shiyu Zhang, Beijing (CN); Jiahui Han, Beijing (CN); Zheng Fang, Beijing (CN); Ge Shi, Beijing (CN); Haijun Niu, Beijing (CN); Yujie Liu, Beijing (CN); Yuyao Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 495 days.

(21) Appl. No.: 16/450,735

(22) Filed: Jun. 24, 2019

(65) Prior Publication Data

US 2020/0150134 A1     May 14, 2020

(30) Foreign Application Priority Data

Nov. 8, 2018  (CN) .......................... 201811327483.0

(51) Int. Cl.
*G01N 35/00* (2006.01)
*B01J 19/00* (2006.01)
(Continued)

(52) U.S. Cl.
CPC .... *G01N 35/00029* (2013.01); *B01J 19/0046* (2013.01); *C12Q 1/6837* (2013.01);
(Continued)

(58) Field of Classification Search
CPC ............ G01N 35/00029; G01N 21/64; G01N 2035/00158; B01J 19/0046;
(Continued)

(56) References Cited

U.S. PATENT DOCUMENTS

| 7,253,006 B2 * | 8/2007 | Takagi ................. B01J 19/0046 422/68.1 |
| 2010/0218834 A1 | 9/2010 | Rasmussen et al. |
| 2019/0360913 A1 * | 11/2019 | Schmidt ............. G01N 15/1459 |

FOREIGN PATENT DOCUMENTS

| CN | 1464071 A | 12/2003 |
| CN | 201060194 Y | 5/2008 |
| CN | 108319096 A | 7/2018 |

OTHER PUBLICATIONS

"First Office Action and English language translation", Chinese Patent Application No. 201811327483.0, dated Apr. 27, 2021, 12 pp.

* cited by examiner

*Primary Examiner* — Narayan K Bhat
(74) *Attorney, Agent, or Firm* — Myers Bigel, P.A.

(57) ABSTRACT

This disclosure provides a gene chip comprising a substrate and at least one positioning device fixed on an upper surface of the substrate, wherein the at least one positioning device is provided with a receiving cavity for receiving a bead, the receiving cavity being arranged on a surface of the at least one positioning device facing away from the substrate, and a cross-sectional area of the receiving cavity is gradually decreased in a direction toward the upper surface of the substrate. This disclosure further provides a gene detection device comprising the gene chip.

17 Claims, 6 Drawing Sheets

(51) Int. Cl.
*C12Q 1/6837* (2018.01)
*C40B 60/02* (2006.01)

(52) U.S. Cl.
CPC ..... *C40B 60/02* (2013.01); *B01J 2219/00596* (2013.01); *B01J 2219/00648* (2013.01); *B01J 2219/00659* (2013.01); *B01J 2219/00722* (2013.01); *B01L 2200/021* (2013.01); *B01L 2200/026* (2013.01); *B01L 2300/0636* (2013.01); *B01L 2300/16* (2013.01); *G01N 2035/00158* (2013.01)

(58) Field of Classification Search
CPC .... B01J 2219/00596; B01J 2219/00648; B01J 2219/00659; B01J 2219/00722; B01J 2219/005; B01J 2219/00702; C12Q 1/6837; C12Q 2563/107; C12Q 2563/149; C40B 60/02; B01L 2200/021; B01L 2200/026; B01L 2300/0636; B01L 2300/16; B01L 3/5085; B01L 2200/0668; B01L 2300/0896
See application file for complete search history.

GENE CHIP AND GENE DETECTION DEVICE

RELATED APPLICATION

This disclosure claims the priority of Chinese patent application No. 201811327483.0 filed on Nov. 8, 2018, the entire disclosure of which is incorporated herein by reference.

TECHNICAL FIELD

This disclosure relates to the field of optical detection, in particular to a gene chip and a gene detection device.

BACKGROUND ART

A gene detection device comprises a gene chip, a bead coated with fluorescent probes, an emitting means and a detecting means. The emitting means emits excitation light to excite the fluorescent probes to emit fluorescent light, and the detecting means receives the fluorescent light and performs detection based on the received fluorescent light. But during this procedure, the gene chip can also reflect the excitation light, which will influence the accuracy of the detection upon ingress into the detecting means. In order to receive the bead, the gene chip is usually provided with holes in its surface for receiving the bead. The surface of the gene chip not provided with holes is perpendicular to the incident excitation light and reflects the excitation light such that the reflected excitation light enters the detecting means in a direction parallel with the incident excitation light. Thus the excitation light received by the detecting means has high intensity and high reflectivity, which will influence the accuracy of the detection.

SUMMARY

According to a first aspect of this disclosure, a gene chip is provided, the gene chip comprising a substrate and at least one positioning device fixed on an upper surface of the substrate, wherein the at least one positioning device is provided with a receiving cavity for receiving a bead, the receiving cavity being arranged on a surface of the at least one positioning device facing away from the substrate, and a cross-sectional area of the receiving cavity is gradually decreased in a direction toward the upper surface of the substrate.

In one embodiment, each of the at least one positioning device comprises a plurality of positioning blocks spaced apart, and the plurality of positioning blocks are arranged in a circle to form the receiving cavity.

In one embodiment, each of the plurality of positioning blocks comprises a plurality of positioning portions, the positioning portions comprising at least part of a side surface of the positioning block, and at least one positioning portion of each positioning block faces the receiving cavity.

In one embodiment, in a direction towards the upper surface of the substrate, the positioning portions gradually approach a central line of the receiving cavity.

In one embodiment, the at least one positioning device comprises a plurality of positioning devices, and two adjacent positioning devices share at least one positioning block.

In one embodiment, each of the plurality of positioning devices comprises six positioning blocks distributed evenly around the central line of the receiving cavity, and two adjacent positioning devices share two adjacent positioning blocks.

In one embodiment, each of the plurality of positioning blocks comprises three positioning portions, each of the three positioning portions comprising at least part of a side surface of the positioning block, and the three positioning portions face three receiving cavities adjacent to each other respectively.

In one embodiment, in a direction towards the upper surface of the substrate, a cross-sectional area of the positioning blocks is gradually increased.

In one embodiment, the gene chip is made of a transparent material.

According to a second aspect of this disclosure, a gene detection device is provided, comprising any of the above gene chips and a bead coated with a fluorescent material, and the bead is fixed in the receiving cavity of the gene chip.

In one embodiment, the bead comprises a metal material.

In one embodiment, the bead comprises a body and a cladding layer, the cladding layer covering an outer surface of the body, a fluorescent material covering an outer side of the cladding layer, and the cladding layer and the substrate of the gene chip are made of a same material.

By providing an angled structure on the surface of the receiving cavity, the gene chip and the gene detection device provided in the embodiments of this disclosure both reduce the reflection of excitation light by the surface of the receiving cavity and increase the exposed area of the bead, thereby increasing the area of the fluorescent probes that can be excited. During the use of the gene chip provided in the embodiments of this disclosure, the proportion of the fluorescent light excited by the fluorescent probes on the bead to the light received by the gene detection device is increased, the accuracy of the detection of the gene chip is improved.

BRIEF DESCRIPTION OF DRAWINGS

The drawings are used to provide further understanding of the embodiments of this disclosure and constitute part of the description. They are intended for explaining the technical solutions of this disclosure in cooperation with the embodiments of this disclosure, rather than limiting this disclosure. Shapes and sizes of components in the drawings do not reflect true ratios, but instead they are only provided to illustrate the content of the disclosure.

DETAILED DESCRIPTION OF EMBODIMENTS

The specific implementation of this disclosure will be further explained in detail with reference to the drawings and the embodiments. The embodiments below are used for explaining this disclosure rather than limiting the scope of this disclosure. It should be noted that the embodiments in this disclosure and the features of the embodiments can be combined with each other randomly under the circumstances that there is no conflict.

In the description of this disclosure, it should be understood that directional or positional relations indicated by terms such as "center", "up", "down", "front", "rear", "vertical", "horizontal", "top", "bottom", "inner" and "outer" are directional or positional relations shown on the basis of the drawings. They are used only for describing this disclosure and simplifying the description, instead of indicating or implying that the indicated devices or elements must be orientated specifically, or constructed and operated in a specific orientation, so they cannot be construed as limiting this disclosure.

In the description of this disclosure, it should be noted that terms of "install", "link" and "connect" should be understood in a broad sense unless otherwise prescribed and defined explicitly. For example, "connect" can refer to fixed connection, or detachable connection, or integrated connection; it can also refer to mechanical connection or electrical connection; or direct connection, or indirect connection via intermediate media, or even connection inside two elements. For a person having ordinary skills in the art, the specific meanings of the above terms in this disclosure can be understood upon specific situations.

As shown in FIGS. 1-6, the embodiments of this disclosure provide a gene detection device, the gene detection device comprises a gene chip 100, a bead 200 located on the gene chip 100 and coated with fluorescent probes 230, an emitting means and a detecting means (the emitting means and the detecting means are not shown). The emitting means emits excitation light to the gene chip 100 and the bead 200 located on the gene chip 100. The fluorescent probes 230 are excited by the excitation light to emit fluorescent light, and meanwhile the gene chip 100 reflects the excitation light. The detecting means receives the excitation light and the fluorescent light, and detects fluorescent signals based on the receive fluorescent light.

Figure 1:
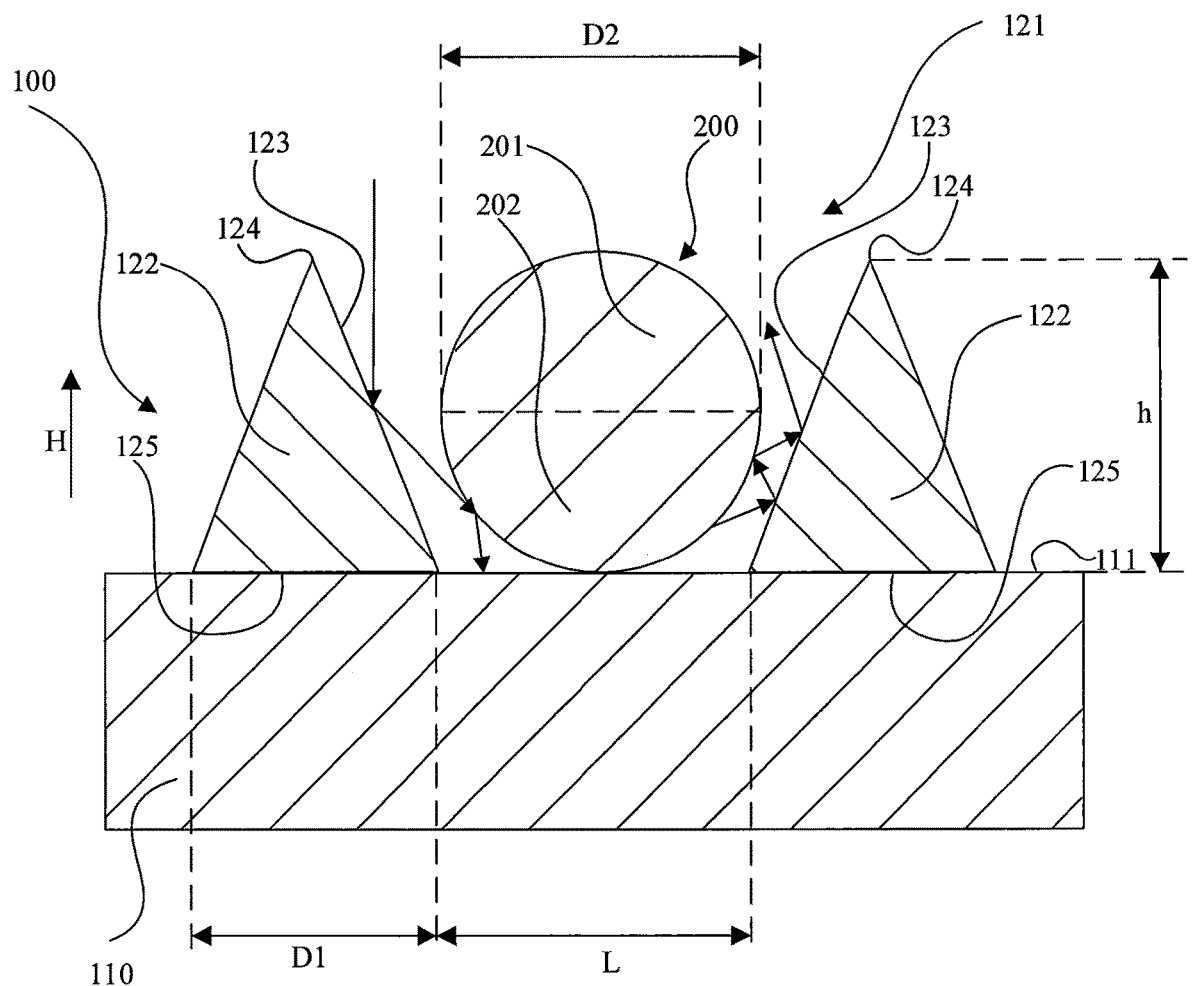
FIG. 1 is a schematic section view of the gene detection device according to an embodiment of this disclosure.
Figure 2:
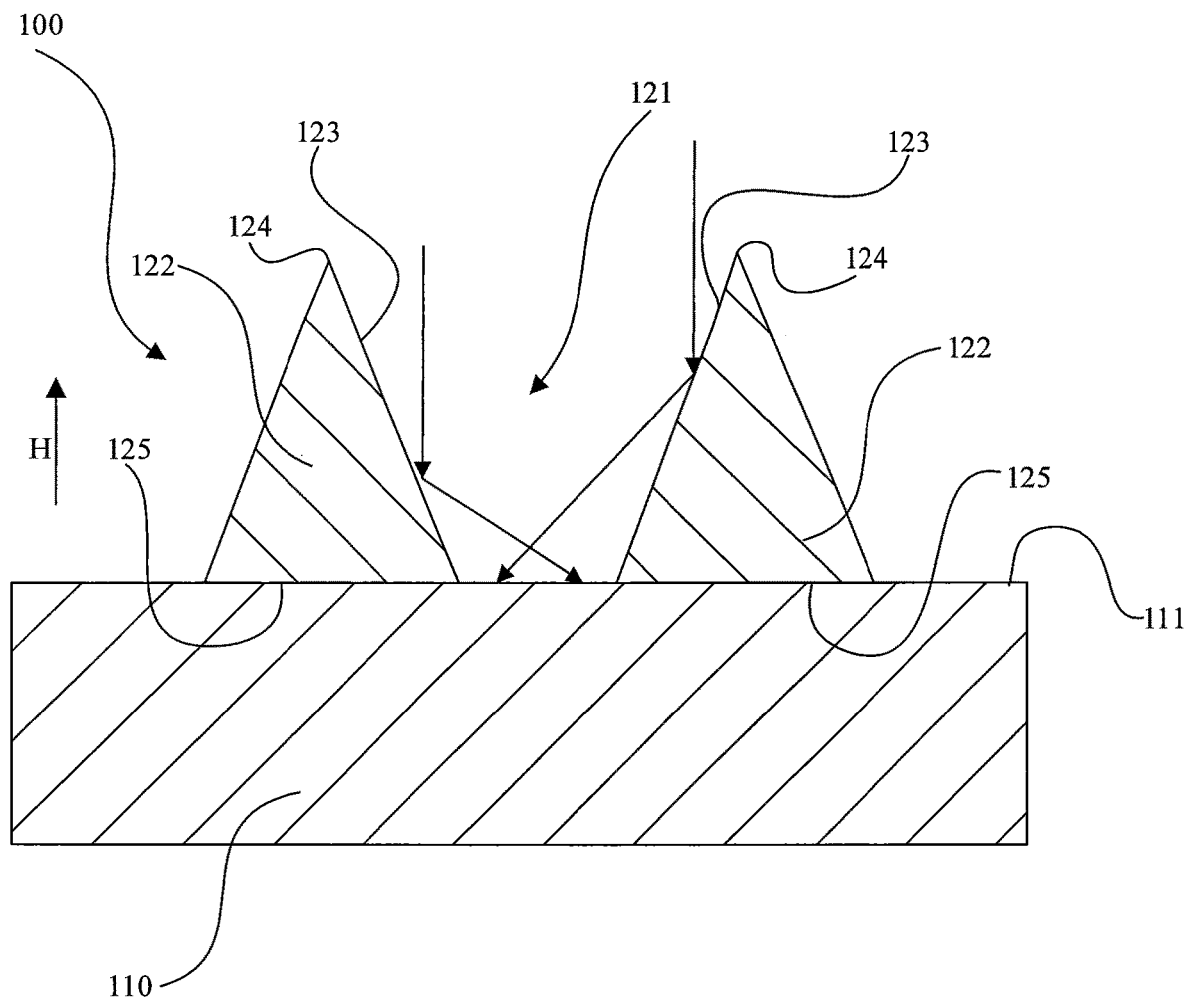
FIG. 2 is a schematic section view of the gene chip according to an embodiment of this disclosure.
Figure 4:
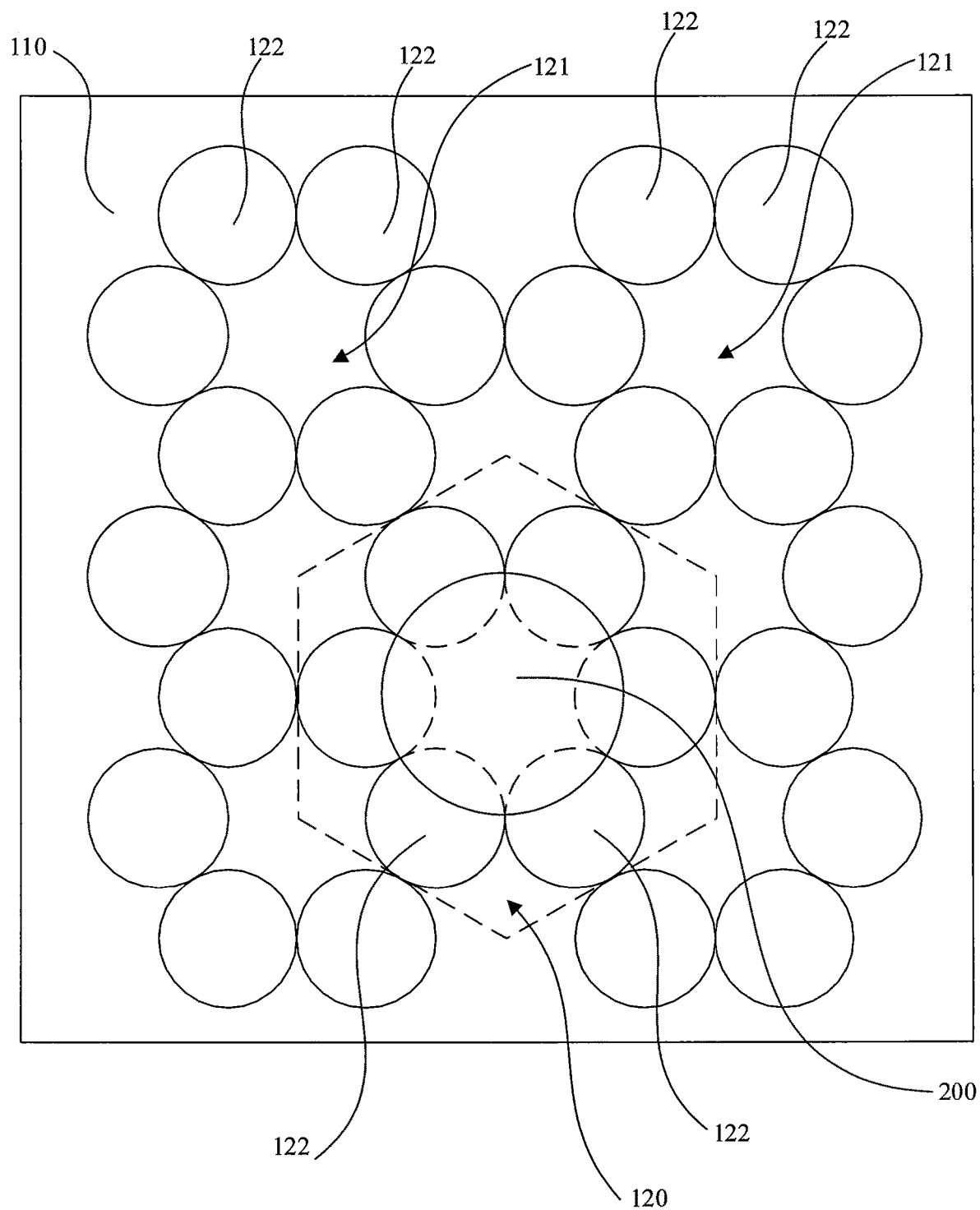
FIG. 4 is a schematic top view of the gene chip according to an embodiment of this disclosure.

As shown in FIGS. 1 and 2, the gene chip 100 comprises a substrate 110 and a positioning device 120 (see FIG. 4). When gene detection is performed using the gene chip 100, it is necessary to place a bead 200 coated with the fluorescent probes 230 into the positioning device 120 of the gene chip 100 and irradiate the gene chip 100 with excitation light. The fluorescent probes 230 are excited by the excitation light to emit fluorescent light, and the detecting means receives the fluorescent light emitted by the fluorescent probes 230 and performs gene detection based on the received fluorescent light.

As shown in FIGS. 1 and 2, the positioning device 120 (see FIG. 4) is fixed on an upper surface 111 of the substrate and provided with a receiving cavity 121. The receiving cavity 121 is used for receiving a bead 200 coated with the fluorescent probes 230 on an outer surface thereof, and the receiving cavity 121 can receive only one bead 200. In this embodiment, as shown in FIG. 1, the bead 200 is positioned by means of the receiving cavity 121. The receiving cavity 121 is arranged on a surface of the positioning device 120 facing away from the substrate 110. In a height direction H of the positioning device 120, a cross-sectional area of the receiving cavity 121 is gradually decreased as it approaches the upper surface 111 of the substrate. The receiving cavity 121 can have an inclined surface. When the gene chip 100 is irradiated by excitation light, the fluorescent probes 230 are excited by the excitation light to emit fluorescent light, and meanwhile the positioning device 120 reflects the excitation light. Therefore, the detecting means can detect not only the fluorescent light, but also the excitation light reflected by the positioning device 120.

As shown in FIG. 2, with the arrangement of an inclined surface, the excitation light received by the detecting means is reduced. Referring to FIG. 2, arrows in the middle of the drawing indicate two incident beams of excitation light, and the excitation light is reflected when arriving at the inclined surface such that the reflected excitation light will not enter the detecting means in a direction parallel with the incident excitation light. Referring to FIG. 1, arrows in the middle left indicate incident excitation light, an inclined surface of the positioning device 120 reflects the incident excitation light towards the bead 200, the excitation light reflected by the inclined surface can directly impinge on a surface of the bead 200 coated with fluorescent probes 230, thereby improving the intensity of fluorescent light emitted by the fluorescent probes 230.

A cross-sectional area of the receiving cavity 121 is gradually decreased in a direction towards the substrate 110 such that the area of the bead 200 exposed to the incident excitation light is greater than 50% of the area of an outer surface of the bead 200. If the bead 200 is divided into an upper sphere 201 and a lower sphere 202, when a side surface of the receiving cavity 121 is a vertical surface, the surface of the bead 200 exposed to the incident excitation light is only a surface of the upper sphere 201; when the surface of the receiving cavity 121 is an inclined surface as shown in FIG. 1, a partial surface of the lower sphere can also be exposed to the incident excitation light, which increases the surface area that can be irradiated by the excitation light, improves the probability that the fluorescent probes 230 will be excited, and enhances the intensity of the excited fluorescent light. The inclined surface of the receiving cavity 121 can reflect part of the excitation light to the surface of the lower sphere 202, which increases the area of the bead 200 irradiated by the excitation light. A height of the receiving cavity 121 can be greater than that of the bead 200. Referring to FIG. 1, arrows in the middle right indicate fluorescent light emitted by the fluorescent probes 230 after being excited. The fluorescent light can be scattered via a gap between the receiving cavity 121 and the bead 200 such that the fluorescent light excited from the lower sphere 202 can enter the detecting means, which enhances the intensity of the excited fluorescent light. With the arrangement of an inclined surface, the proportion of fluorescent light received by the detecting means can be increased, and the accuracy of the detection can be improved. Besides, the inclined surface facilitates the successful ingress of the bead 200 into the receiving cavity 121 for positioning.

Figure 5:
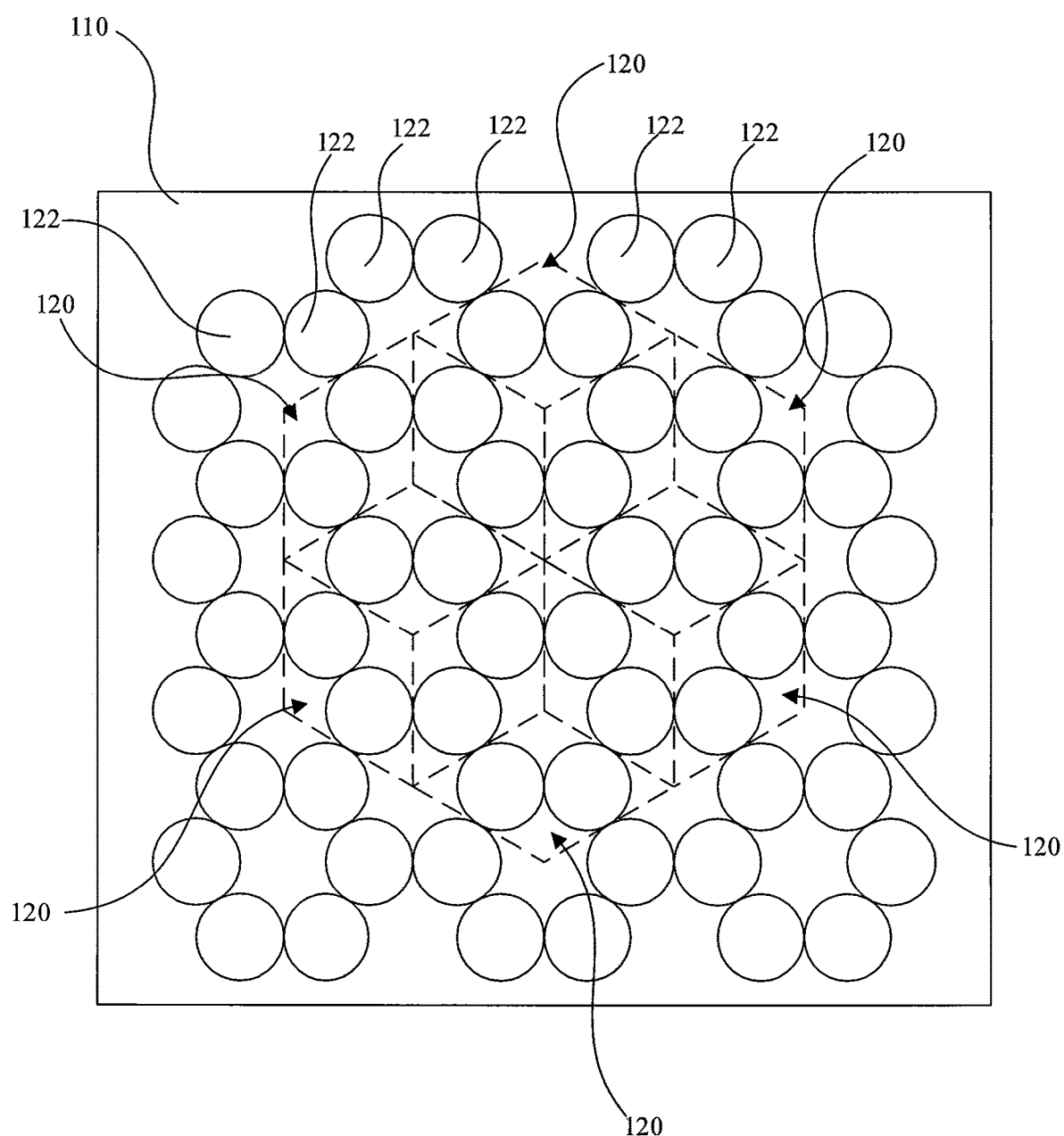
FIG. 5 is a schematic top view of the gene chip according to an embodiment of this disclosure.

As shown in FIGS. 1-6, the positioning device 120 can comprise a plurality of positioning blocks 122 spaced apart, and the positioning blocks 122 are arranged in a circle to form the receiving cavity 121. The manner in which the plurality of positioning blocks 122 are spaced apart facilitates the flow of a liquid carrying the bead 200. As shown in FIGS. 4 and 5, there can be six positioning blocks 122, and in other embodiments, there can be two to five, seven or more than seven positioning blocks 122.

As shown in FIGS. 1 and 2, the positioning block 122 comprises a plurality of positioning portions 123. The positioning portion 123 can comprise at least part of a side surface of the positioning block 122. At least one positioning portion 123 of each positioning block 122 faces the receiving cavity 121, and the plurality of positioning portions 123 can form the surface of the receiving cavity 121. In a direction towards the upper surface 111 of the substrate, the positioning portions 123 gradually approach is a central line of the receiving cavity 121 so as to form a receiving cavity 121 with a cross-sectional area gradually decreased. When the area of an upper surface 124 of the positioning block 122 is smaller than that of the lower surface 125 of the positioning block, the area of the upper surface 124 of the positioning block 122 perpendicular to the incident direction of the excitation light is decreased, which reduces the ingress of the excitation light reflected by the upper surface 124 into the detecting means and diminishes the background stray light.

In one embodiment, two adjacent positioning devices 120 can share at least one positioning block 122 as shown in FIG. 5. With such an arrangement, the utilization of the positioning block 122 can be improved such that more beads 200 can be received in a gene chip 100 having the same size and the same number of positioning blocks 122. As shown in FIGS. 4 and 5, in this embodiment, the positioning device 120 comprises six positioning blocks 122 arranged in a hexagon, which ensures that the beads 200 can be arranged in the densest manner and thereby increases the utilization of the substrate 110.

As shown in FIG. 4, the dashed box portion shows a positioning device 120. As shown in FIG. 5, the dashed box portion shows six positioning devices 120 adjacent to a central positioning device, and any two adjacent positioning devices 120 share two positioning blocks 122. In this case, each positioning block 122 comprises three positioning portions 123 distributed evenly which face three receiving cavities 121 adjacent to each other respectively.

Figure 3:
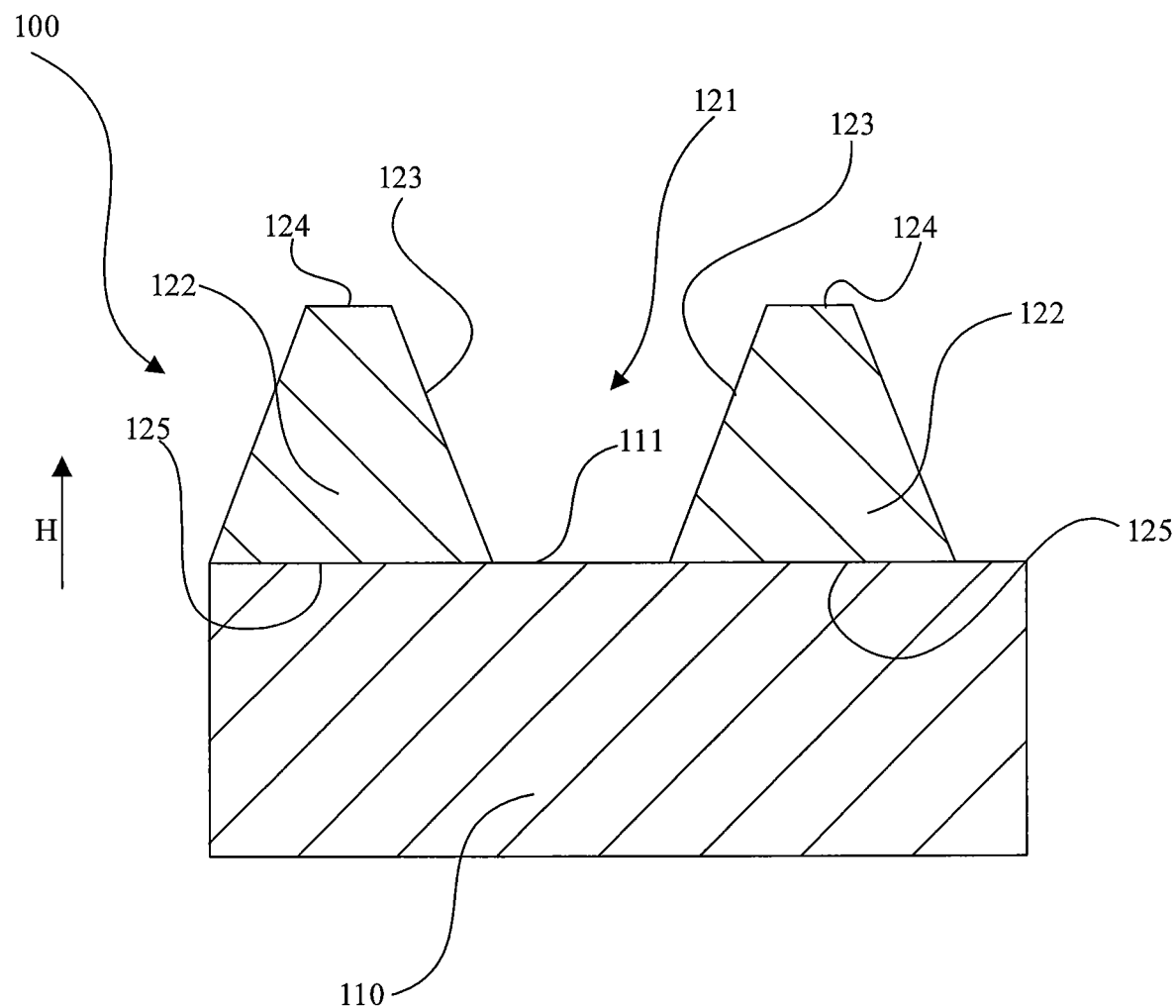
FIG. 3 is a schematic section view of the gene chip according to an embodiment of this disclosure.

As shown in FIGS. 1, 2, 4 and 5, in this embodiment, the positioning block 122 may have a cone shape, and a side surface of the positioning block 122 is evenly divided into three positioning portions 123. By arranging the shape of the positioning block 122 to be conical, the area of the upper surface 124 of the positioning device 120 is decreased to the maximum degree, and in turn the excitation light reflected by the upper surface 124 of the positioning device 120 is decreased to reduce the reflectivity of the excitation light. Experiments have shown that when the side surface of the receiving cavity 121 is a vertical surface, the reflectivity of the excitation light is 35%, and when the positioning block 122 is formed in a cone shape, the reflectivity of the excitation light is reduced to 17%. By reducing the reflection of the excitation light by the positioning device 120, the background stray light can be decreased, and thus the interference of the background stray light to the fluorescent light excited from the fluorescent probes 230 can be diminished and the contrast of the fluorescent light can be improved. In other embodiments, as shown in FIG. 3, the positioning block 122 may also have a truncated cone shape, and the upper surface 124 of the positioning block 122 is smaller than the lower surface 125 of the positioning block 122.

Referring to FIG. 1, in an embodiment, the positioning block 122 has a height h of 400 nm and a bottom diameter D1 of 500 nm, and two adjacent positioning blocks are spaced by a minimum distance L of 1300 nm, and the bead 200 has a diameter D2 of 1300 nm. In order to better reflect the optical path of the incident light, the optical path of the excited fluorescent light, and the structures of the positioning device and the substrate, the sizes of the positioning block 122, the bead 200, and the substrate 110 are not drawn to a true scale. Besides, the above sizes can be adjusted upon specific needs.

In one embodiment, the gene chip 100 is made of a transparent material, i.e., the substrate 110 and the positioning device 120 are both made of a transparent material. With such an arrangement, the reflectivity of the positioning device 120 and the substrate 110 with respect to the excitation light is reduced. The material of the gene chip 100 may also comprise glass or resin, or other transparent materials that can be easily nano-imprinted.

In an embodiment, the substrate 110 and the positioning device 120 are separable parts so as to facilitate cleaning when the gene chip 100 is used repeatedly. However, this disclosure is not limited thereto, and the substrate 110 and the positioning device 120 may also be formed integrally.

Figure 6:
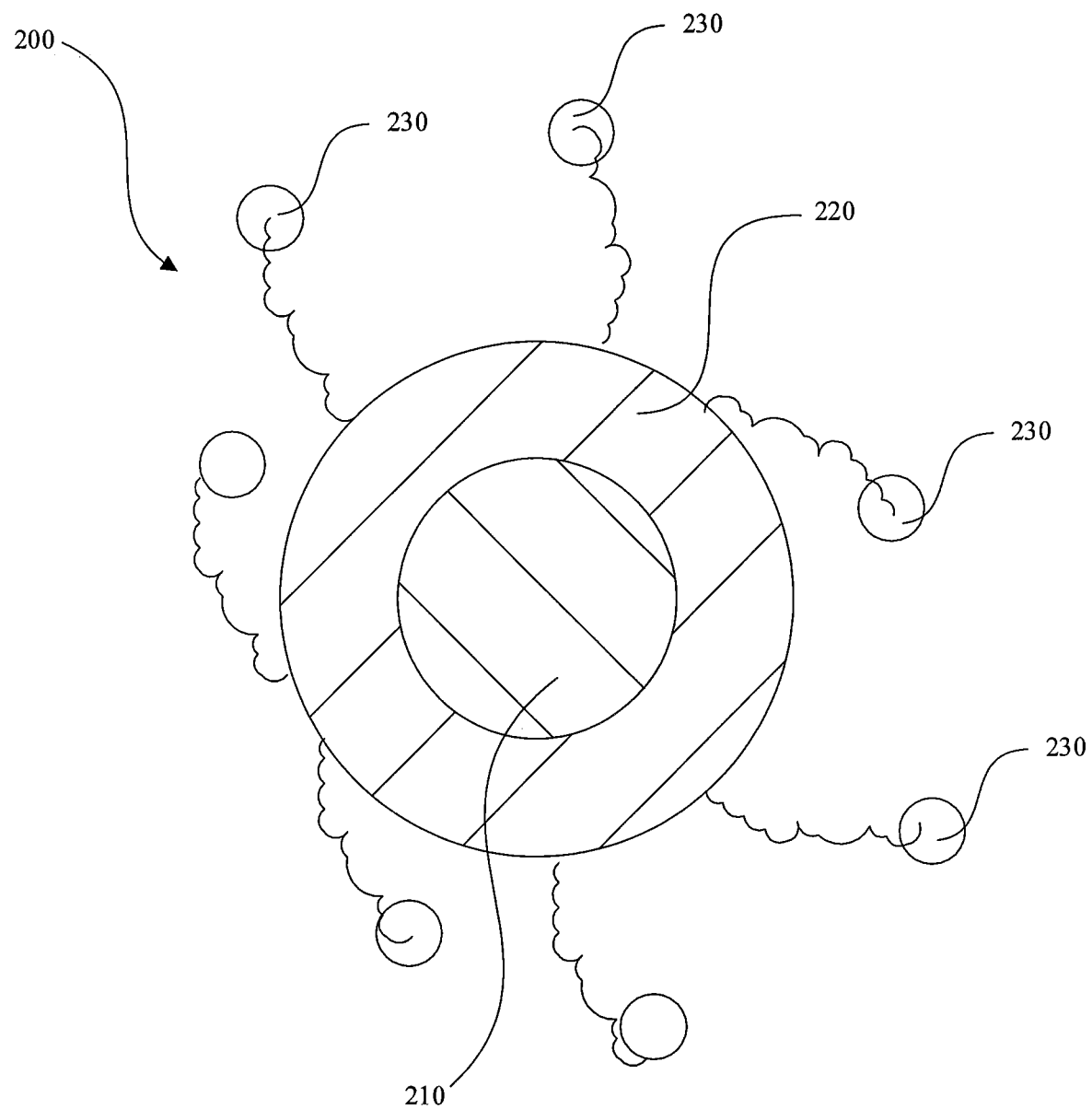
FIG. 6 is a schematic section view of the bead according to an embodiment of this disclosure.

As shown in FIG. 6, the bead 200 comprises a portion made of a metal material. For example, a body 210 of the metal material can cause localized surface plasmon resonance, and the metal material can facilitate excitation of the fluorescent probes 230. In an embodiment, the bead 200 comprises a body 210 and a cladding layer 220 covering an outer surface of the body 210. With such an arrangement, simulation results show that the Purcell factor is 1.18, so the intensity of the fluorescent light excited from the fluorescent probes 230 can be enhanced by 18%. The material of the body 210 can comprise gold, silver, copper, aluminum or other metal materials. The material of the cladding layer 220 can be the same as that of the substrate 110. When the material of the cladding layer 220 is the same as that of the substrate 110, there is a van der Waals force between the bead 200 and the surface of the receiving cavity 121 or between the bead 200 and the surface of the substrate 110, which facilitates fixation of the bead 200. The fluorescent probes 230 may cover an outer side of the cladding layer 220, and the cladding layer 220 can prevent the body 210 of the bead 200 made of a metal material from being brought into direct contact with the fluorescent probes 230, thereby avoiding quenching of the fluorescent substance of the fluorescent probes 230. Since the material of the cladding layer 220 is the same as that of the gene chip 100, an amino group or a thiol group which forms a covalent bond with DNA can be directly synthesized on the surface of the cladding layer 220, and gene probes having a fluorescent substance (i.e., fluorescent probes 230) can be implanted. In an embodiment, the cladding layer 220 may have a thickness of 150 nm, which can be adjusted upon actual needs. In order to clearly render the structures of the cladding layer 220 and the body 210, the sizes of the cladding layer 220 and the body 210 are not drawn to a true scale.

Although the implementations of this disclosure are disclosed above, the contents thereof only relate to implementations adopted for understanding this disclosure instead of limiting this disclosure. Any skilled person in the art of this disclosure can make any modifications and variations in terms of forms and details of the implementations without deviating from the spirits and scopes disclosed in this disclosure. The protection scope of this disclosure is subjected to the scope defined in the appended claims.

The invention claimed is:

1. A gene chip, comprising:
a substrate; and
at least one positioning device fixed on an upper surface of the substrate,
wherein the at least one positioning device comprises a receiving cavity configured to receive a bead,
wherein the receiving cavity is arranged on a surface of the at least one positioning device facing away from the substrate,
wherein a cross-sectional area of the receiving cavity is decreased in a direction toward the upper surface of the substrate, wherein each of the at least one positioning device comprises a plurality of positioning blocks spaced apart, and
wherein the plurality of positioning blocks are in a circle to form the receiving cavity.

2. The gene chip according to claim 1,
wherein each of the plurality of positioning blocks comprises a plurality of positioning portions,
wherein the positioning portions comprise at least part of a side surface of a respective positioning block of the plurality of positioning blocks, and
wherein at least one positioning portion of the plurality of positioning portions of each positioning block faces the receiving cavity.

3. The gene chip according to claim 2, wherein in a direction towards the upper surface of the substrate, the plurality of positioning portions approach a central line of the receiving cavity.

4. The gene chip according to claim 1,
wherein the at least one positioning device comprises a plurality of positioning devices, and
wherein adjacent ones of the at least one positioning device share at least one positioning block.

5. The gene chip according to claim 4,
wherein each of the plurality of positioning devices comprises six positioning blocks distributed evenly around a central line of the receiving cavity, and
wherein the adjacent ones of the at least one positioning device share two adjacent positioning blocks.

6. The gene chip according to claim 5,
wherein each of the plurality of positioning blocks comprises three positioning portions,
wherein each of the three positioning portions comprises at least part of a side surface of a respective positioning block of the plurality of positioning blocks, and
wherein the three positioning portions face three receiving cavities adjacent to each other respectively.

7. The gene chip according to claim 5,
wherein in a direction towards the upper surface of the substrate, a cross-sectional area of the positioning blocks is increased.

8. The gene chip according to claim 1, wherein the gene chip comprises a transparent material.

9. A gene detection device comprising:
a gene chip; and
a bead coated with a fluorescent material,
wherein the gene chip comprises a substrate and at least one positioning device fixed on an upper surface of the substrate,
wherein the at least one positioning device comprises a receiving cavity configured to receive the bead,
wherein the receiving cavity is arranged on a surface of the at least one positioning device facing away from the substrate,
wherein a cross-sectional area of the receiving cavity decreases in a direction toward the upper surface of the substrate,
wherein the bead is fixed in the receiving cavity,
wherein each of the at least one positioning device of the gene chip comprises a plurality of positioning blocks spaced apart, and
wherein the plurality of positioning blocks are in a circle to form the receiving cavity.

10. The gene detection device according to claim 9,
wherein each of the plurality of positioning blocks comprises a plurality of positioning portions,
wherein the positioning portions comprise at least part of a side surface of a respective positioning block of the plurality of positioning blocks, and
wherein at least one positioning portion of each of the plurality of positioning blocks faces the receiving cavity.

11. The gene detection device according to claim 10, wherein in a direction towards the upper surface of the substrate, the plurality of positioning portions approach a central line of the receiving cavity.

12. The gene detection device according to claim 9,
wherein the at least one positioning device of the gene chip comprises a plurality of positioning devices, and
wherein two adjacent positioning devices of the plurality of positioning devices share at least one positioning block.

13. The gene detection device according to claim 12,
wherein each of the plurality of positioning devices comprises six positioning blocks of the plurality of positioning blocks distributed around a central line of the receiving cavity, and
wherein the two adjacent positioning devices share two adjacent positioning blocks of the plurality of positioning blocks.

14. The gene detection device according to claim 13,
wherein each of the plurality of positioning blocks comprises three positioning portions,
wherein each of the three positioning portions comprises at least part of a side surface of a respective positioning block of the plurality of positioning blocks, and
wherein the three positioning portions face three receiving cavities adjacent to each other respectively.

15. The gene detection device according to claim 13, wherein in a direction towards the upper surface of the substrate, a cross-sectional area of the positioning blocks is increased.

16. The gene detection device according to claim 9, wherein the gene chip comprises a transparent material and the bead comprises a metal material.

17. The gene detection device according to claim 16,
wherein the bead comprises a body and a cladding layer,
wherein the cladding layer overlaps an outer surface of the body,
wherein a fluorescent material overlaps an outer side of the cladding layer, and
wherein the cladding layer and the substrate comprise a same material.

* * * * *